United States Patent
Lynk (10) Patent No.: US 10,190,949 B2
(45) Date of Patent: Jan. 29, 2019

(54) METHOD AND APPARATUS FOR A CONE PENETRATION TEST WITH WHIPSTOCK-ENABLED SOIL SAMPLING

(71) Applicant: John M. Lynk, Houston, TX (US)

(72) Inventor: John M. Lynk, Houston, TX (US)

( * ) Notice: Subject to any disclaimer, the term of this patent is extended or adjusted under 35 U.S.C. 154(b) by 104 days.

(21) Appl. No.: 15/629,456

(22) Filed: Jun. 21, 2017

(65) Prior Publication Data

US 2018/0010987 A1 Jan. 11, 2018

Related U.S. Application Data

(60) Provisional application No. 62/360,376, filed on Jul. 9, 2016.

(51) Int. Cl.
| | | |
|---|---|---|
| *G01N 1/08* | (2006.01) | |
| *G01N 3/06* | (2006.01) | |
| *G01N 3/42* | (2006.01) | |
| *G01N 33/24* | (2006.01) | |

(Continued)

(52) U.S. Cl.
CPC ............... *G01N 1/08* (2013.01); *G01N 3/066* (2013.01); *G01N 3/42* (2013.01); *G01N 33/24* (2013.01); *G05B 19/048* (2013.01); *G01N 2035/00881* (2013.01); *G01N 2203/0016* (2013.01); *G05B 2219/23269* (2013.01); *G05B 2219/24015* (2013.01)

(58) Field of Classification Search
CPC ............ G01N 1/08; G01N 3/066; G01N 3/42; G01N 33/24; G01N 2035/00881; G01N 2203/0016; G05B 19/048; G05B 2219/23269; G05B 2219/24015
See application file for complete search history.

(56) References Cited

U.S. PATENT DOCUMENTS

| | | |
|---|---|---|
| 4,252,220 A | 2/1981 | Peterson |
| 4,411,160 A | 10/1983 | Lutenegger et al. |
| 5,307,884 A | 5/1994 | Millgard |

(Continued)

FOREIGN PATENT DOCUMENTS

| | | |
|---|---|---|
| JP | H 11303055 | 2/1999 |
| JP | H 11117279 | 4/1999 |

(Continued)

OTHER PUBLICATIONS

Gouda Geo-Equipment B.V., Window Type Soil Samplers for CPT (www.gouda-geo.com article accessed Jul. 2, 2017).

(Continued)

*Primary Examiner* — Ryan D Walsh
(74) *Attorney, Agent, or Firm* — Peter L. Brewer; Thrive IP (57) ABSTRACT

A method and apparatus for geotechnical soil sampling in conjunction with the Cone Penetration Test (CPT) is provided. The apparatus involves a tubular whipstock cell affixed between push rods and the lower elements of a cone penetrometer. The whipstock cell includes a whipstock having a beveled face. The whipstock face is oriented towards a sampling window pre-formed in the whipstock cell. The apparatus also includes at least one push rod connected to the proximal end of the whipstock cell, and an elongated sampling rod dimensioned to be slidably moved through the at least one push rod en route to the whipstock cell. The apparatus additionally comprises a soil sampler residing at a distal end of the push rod. A method of taking soil samples is also provided herein.

21 Claims, 8 Drawing Sheets

(51) Int. Cl.
*G01N 35/00* (2006.01)
*G05B 19/048* (2006.01)

(56) References Cited

U.S. PATENT DOCUMENTS

| | | | |
|---|---|---|---|
| 5,358,057 A | 10/1994 | Peters et al. | |
| 5,902,939 A | 5/1999 | Ballard et al. | |
| 5,921,328 A | 7/1999 | Babineau et al. | |
| 6,097,785 A * | 8/2000 | Elam | G01N 23/223 250/253 |
| 2017/0370064 A1* | 12/2017 | Morgan | E02D 1/027 |

FOREIGN PATENT DOCUMENTS

| | | |
|---|---|---|
| JP | H 11140858 | 5/1999 |
| JP | 2003/041564 | 2/2003 |
| JP | 2011/226157 | 11/2011 |
| JP | 2012/172484 | 9/2012 |
| JP | 2014/173398 | 9/2014 |

OTHER PUBLICATIONS

Hole Products, Other Soil Samplers (www.holeproducts.com webpage article accessed Jul. 2, 2017).
Geoprobe, DT22 Soil Sampling System product brochure.
Vertek, Vertek ConeSipper CPT (www.environmental-expert.com webpage article accessed Jul. 2, 2017).
Cone Penetration, In-Situ Soil Testing (www.conepenetration.com webpage article accessed Jul. 2, 2017).
AMS Soil Probes, Soil Probes (www.ams-samplers.com webpage article accessed Jul. 2, 2017).

\* cited by examiner

METHOD AND APPARATUS FOR A CONE PENETRATION TEST WITH WHIPSTOCK-ENABLED SOIL SAMPLING

CROSS REFERENCE TO RELATED APPLICATIONS

This application claims the benefit of U.S. Ser. No. 62/360,376 filed Jul. 7, 2016. That application is entitled "Method and Apparatus For A Cone Penetration Text [sic] With Whipstock-Enabled Soil Sampling," and is incorporated by reference herein in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

FIELD OF THE INVENTION

The present invention relates to the field of geotechnical soil investigations. More specifically, the invention relates to an improved cone penetration apparatus, and method for conducting a soil cone penetration test.

Discussion of Technology

Geotechnical soil investigations are frequently conducted to assess the structural properties of rocks and soil. For example, civil engineers will conduct geotechnical analysis of an underburden before constructing buildings, bridges, roads, dams or other engineered improvements.

As part of the geotechnical analysis, engineers will take soil and rock samples from the area under consideration. One device used for taking such samples is a so-called cone penetrometer. A cone penetrometer includes a cone tip that penetrates through soil and the near-surface strata below. Cone penetrometers may also include a friction sleeve, a threaded connection to push rods from the surface, and a wire that transmits data back to the surface in real time. In some instances, a cone penetrometer may include piezoelectric pore pressure gauges, wireless communication systems, and sonic measuring tools.

Cone penetrometers are used in connection with a so-called Cone Penetration Test. The Cone Penetration Test (CPT) is covered by standard ASTM Test Method D 5778. To conduct a CPT, the cone tip is urged into soil at a designated location using a strong downward force. The force is transmitted through rods threadedly connected end-to-end. As the cone penetrates the soil and the subsurface below, resistance data from the cone tip and the attached friction sleeve is returned to the surface. Other data such as moisture content and pore pressure may be transmitted as well. Of significance, no soil sample is captured and retrieved to the surface during a CPT, as documented in ASTM Test Method D 5778.

A separate test sometimes used by civil engineers is the Standard Penetration Test (SPT). The SPT is a method of soil testing in which soil samples are brought back to the surface. In an SPT, an auger is rotated through a soil deposit of interest. A split spoon is then driven through the center of the auger to take a soil sample The split spoon is activated from the surface to obtain a subsurface soil sample. The soil sample is then extracted to the surface such as by means of a cable.

In connection with the SPT, the auger may optionally be rotated further downwards into the soil deposit after a first sample is captured. The split spoon is then used again to capture another soil sample. This process may be repeated to obtain a desired number of soil samples at desired depths before the split spoon is extracted. The SPT is covered by ASTM D 1586.

An advantage of the CPT over the SPT is that it provides continuous soil data. For the CPT, engineering data is obtained continuously over the full depth of the soil deposit of interest, as the cone tip and friction sleeve provide continuous force measurements and, optionally, in situ data. However, for the SPT, engineering data is obtained only at those intervals where split spoon sampling has occurred and only upon retrieval of the soil at the surface. Of course, for a given soil deposit of a given depth, the SPT typically takes more time to conduct than the CPT. In addition, with the SPT test method, there is a risk of not sampling weak soil intervals, which may detract from the integrity of subsequent engineering designs.

In some soil sampling procedures, an avulsive soil sample is required. An avulsive soil sample is one where the sample is kept intact, that is, as it resided in situ. In connection with the ASTM D 2937-00—Standard Test for Density of Soil in Place by the Drive-Cylinder Method—this is important because the dimensions of the sample need to be taken to measure density. In connection with ASTM D 2850-03a—Standard Test Method for Unconsolidated-Undrained Tri-axial Compression Test on Cohesive Soils—this is important because the strength of the soil fabric is measured by compressing and shearing the intact sample.

A need exists for a soil sampling apparatus that operates with a cone penetrometer while conducting a CPT test, and that allows for multiple whole soil samples to be taken from boreholes. A need further exists for a Cone Penetrometer having a cone tip and a friction sleeve and which permits periodic soil sampling at selected intervals of a soil strata. A need further exists for a cone penetrometer testing apparatus that enables soil testing as with a known CPT, but with the additional benefit of being able to capture and bring to surface multiple soil samples from the same boring location in which the CPT was conducted, while withdrawing the testing apparatus from the ground.

SUMMARY OF THE INVENTION

An apparatus for taking soil samples within a soil boring is provided. Preferably, the apparatus is used in conjunction with a cone penetration testing apparatus to enable the taking of soil samples having penetrated the soil for a CPT and while withdrawing the apparatus back to the surface.

In one aspect, the soil sampling apparatus first comprises an elongated whipstock cell. The whipstock cell defines a tubular body having a proximal end and a distal end. The whipstock cell includes a through-opening placed along a portion of its tubular body. The through-opening provides a pre-formed window through which soil sampling is conducted.

The soil sampling apparatus also includes a whipstock. The whipstock resides within the whipstock cell. The whipstock has a face that is angled towards the pre-formed window. In one aspect, the whipstock defines a solid beveled object residing within the tubular whipstock cell. The whipstock is configured to provide a two-dimensional plane that allows full access at the proximal end of the whipstock cell and no access or limited access at the distal end.

The soil sampling apparatus additionally includes at least one push rod. The at least one push rod may comprise a series of steel joints threadedly connected end-to-end. The lowest push rod is connected to the proximal end of the whipstock cell.

The soil sampling apparatus further includes an elongated sampling rod. The sampling rod may also comprise a series of steel joints threadedly connected end-to-end. The sampling rod is dimensioned to be slidably moved through the at least one push rod en route to the whipstock cell. Thus, the sampling rods have an outer diameter that is smaller than the inner diameter of the elongated push rods.

The soil sampling apparatus also includes a soil sampler. The soil sampler is configured to extend through the pre-formed window. In one aspect, the soil sampler comprises a collar, two opposing spoon elements and a cutting shoe. The cutting shoe resides on a distal end of the sampler and serves as a shearing element to separate soil from a soil strata. The collar resides on the proximal end of the sampler and serves to keep the spoon elements unified during sampling.

The soil sampling apparatus next includes the bent sub. The bent sub has a proximal end and a distal end. The proximal end is connected to a distal end of the sampling rod, while the distal end is connected to the soil sampler by means of the collar of the soil sampler. The bent sub is configured to deflect off of the whipstock face when urged through the pre-formed window. The bent sub may, in one aspect, be a bendable sub, or may be a straight sub having a pliable connection.

The soil sampling apparatus preferably includes a cone penetrometer. The cone penetrometer resides at or below a distal end of the whipstock cell, and will include a friction sleeve. Preferably, the cone penetrometer will also include an associated data cache for storing data concerning rotational and longitudinal force experienced by the cone during soil penetration. The cone penetrometer may also comprise a micro-processor or on-board chip that receives signals indicative of subsurface data. That data may be transmitted up-hole by means of a wire running along or through the at least one push rod. Alternatively, that data may be stored in memory and then uploaded at the surface.

The cone penetrometer will also include a conical tip. The conical tip is connected to the friction sleeve, and is configured to penetrate one or more soil layers in response to force applied through the elongated rod. In operation, the elongated rod is connected to other hollow elongated rods at its proximal end, referred to as the push rods. This allows the conical tip to be advanced within a soil deposit under compressive force from the surface.

In operation, the sampling rods transmit both compressive and tensile forces to the bent sub. In one embodiment, the forces are parallel to the longitudinal axis of the sampling rods. In another aspect, the forces are applied at a slight deviation to the longitudinal axis.

BRIEF DESCRIPTION OF THE DRAWINGS

So that the present inventions can be better understood, certain drawings are appended hereto. It is to be noted, however, that the drawings illustrate only selected embodiments of the inventions and are therefore not to be considered limiting of scope, for the inventions may admit to other equally effective embodiments and applications.

FIG. 4 shows a soil sampling apparatus.

FIG. 5B presents four separate embodiments of a bent sub as may be used in the cone penetrometer of FIG. 3. These are presented as FIGS. 5B-1, 5B-2, 5B-3 and 5B-4.

DETAILED DESCRIPTION OF CERTAIN EMBODIMENTS

Figure 1:
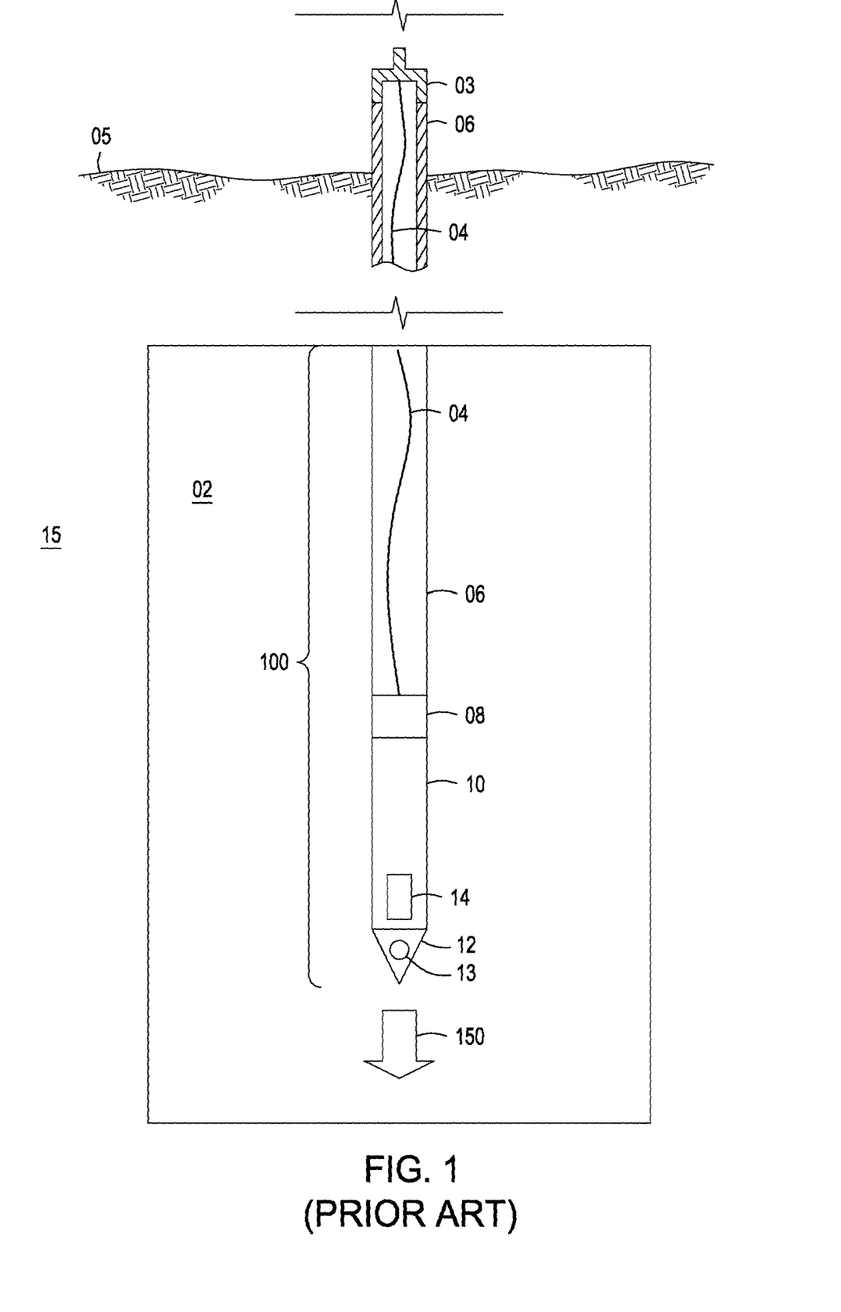
FIG. 1 is a longitudinal side view of a cone penetrometer as is used in a known CPT. Push rods are visible at the top of the drawing.

FIG. 1 is a longitudinal side view of a cone penetrometer 100 as is used in a known Cone Penetration Test. The cone penetrometer 100 is being pushed into a subsurface zone 15 that is under study. Arrow 150 demonstrates a direction of movement of the cone penetrometer 100 during soil testing.

The cone penetrometer 100 is being urged downwardly through a soil strata 2. The strata 2 includes near-surface layers of soil, gravel and/or rock. The downward force is being applied through a tubular body known as a push rod 6. The push rod is seen in cross section, extending from a surface 5 and down into the strata 2.

The cone penetrometer 100 first includes one or more push rods 6. As is outlined in ASTM Test Method D 5778, push rods 6 are "the thick-walled tubes or rods used to advance the penetrometer tip." The push rods 6 are used to receive compressive and tensile forces from a surface rig, and transmit those forces to a cone tip 12. The push rods 6 are also optionally capable of transmitting torque.

The push rods 6 define solid cylindrical elements typically threaded at either end. The function of the push rods 6 in a geotechnical soil investigation is to transmit translational (or longitudinal) and rotational forces from the surface to subsurface testing elements such as sensors. A hydraulic ram 3 is used to advance the push rods 6 into and through the zone of study 15.

The cone penetrometer 100 also includes a wire 4. The wire 4 contains a core with electrically conductive material such as copper, and an outer insulating coating such as plastic. The wire 4 may also contain a non-conductive tensile element to provide tensile strength within its core. The wire 4 transmits electrical signals from the cone penetrometer sensors up to the surface. These electrical signals convey multiple types of data such as cone force data, friction sleeve force data, piezometer pressure data, and acoustic wave travel-time data.

Alternatively or in addition to a wire 4, the cone penetrometer 100 may contain an embedded digital data cache 14. This device stores data that would otherwise be transmitted through a wire 4, and is retrievable at the conclusion of a soil testing event. Data may then be uploaded. The data cache 14 is preferably a micro-processor having flash memory or a RAM cache.

The cone penetrometer 100 also includes a friction sleeve 10. As is outlined in ASTM Test Method D 5778, the friction sleeve 10 is "an isolated cylindrical sleeve section on a penetrometer tip upon which the friction component of penetration resistance develops." The friction sleeve 10 has a surface area of 150 $cm^2$ for 10-$cm^2$ cone tips, or 225 $cm^2$ for 15-$cm^2$ tips. The friction sleeve 10 is reacted upon by passing soil as it is urged downwardly into the soil strata 2 within the zone of study 15 and is connected to a load cell that records soil friction data. This data is used to make correlations regarding soil strength and type.

The cone penetrometer 100 also includes a threaded connection 8. The threaded connection 8 may consist of a frusto-conical shape with ridges forming threads, such that a convex cone with ridges forming mating threads can be abutted and rotated clockwise to form a union. Alternatively, the threaded connection 8 may be a so-called nipple, defining a cylindrical body with internal threads that connects to male pins at opposing ends. The threaded connection 8 connects the push rods 6 to the lower portion of the cone penetrometer 100 (preferably, the friction sleeve 10) such that longitudinal and rotational forces can be transferred from the push rods 6 to the lower elements of the cone penetrometer 100.

The cone penetrometer 100 also includes a cone tip 12. As is outlined in ASTM Test Method D 5778, the cone tip 12 is "the conical point of a cone penetrometer on which the end bearing component of penetration resistance is developed. The cone tip 12 has a 60 degree apex angle, a diameter of 35.7 mm, and a corresponding projected (horizontal plane) surface area or cone base area of 10 $cm^2$. Also, enlarged cones of 43.7 mm diameter (base area=15 $cm^2$) are utilized." As shown, the cone tip 12 resides at a distal end of the friction sleeve 10. The cone tip 12 is reacted upon by soil along strata 2 as the cone tip 12 is urged downwardly into the soil strata 2 along the zone of study 15.

The cone tip 12 is connected to a load cell 13. The load cell 13 records soil reaction force during cone tip 12 movement. This data is also used to make correlations regarding soil strength and type.

As noted above, the cone penetrometer 100 has no ability to capture actual soil samples. Instead, the cone penetrometer 100 takes measurements of subsurface conditions and load cell 13 readings, requiring the geologist or geological engineer to infer soil conditions in the zone of study 15.

Accordingly, it is desirable to redesign a cone penetrometer that enables the geological engineer to visually evaluate soil at multiple sample levels.

Figure 2:
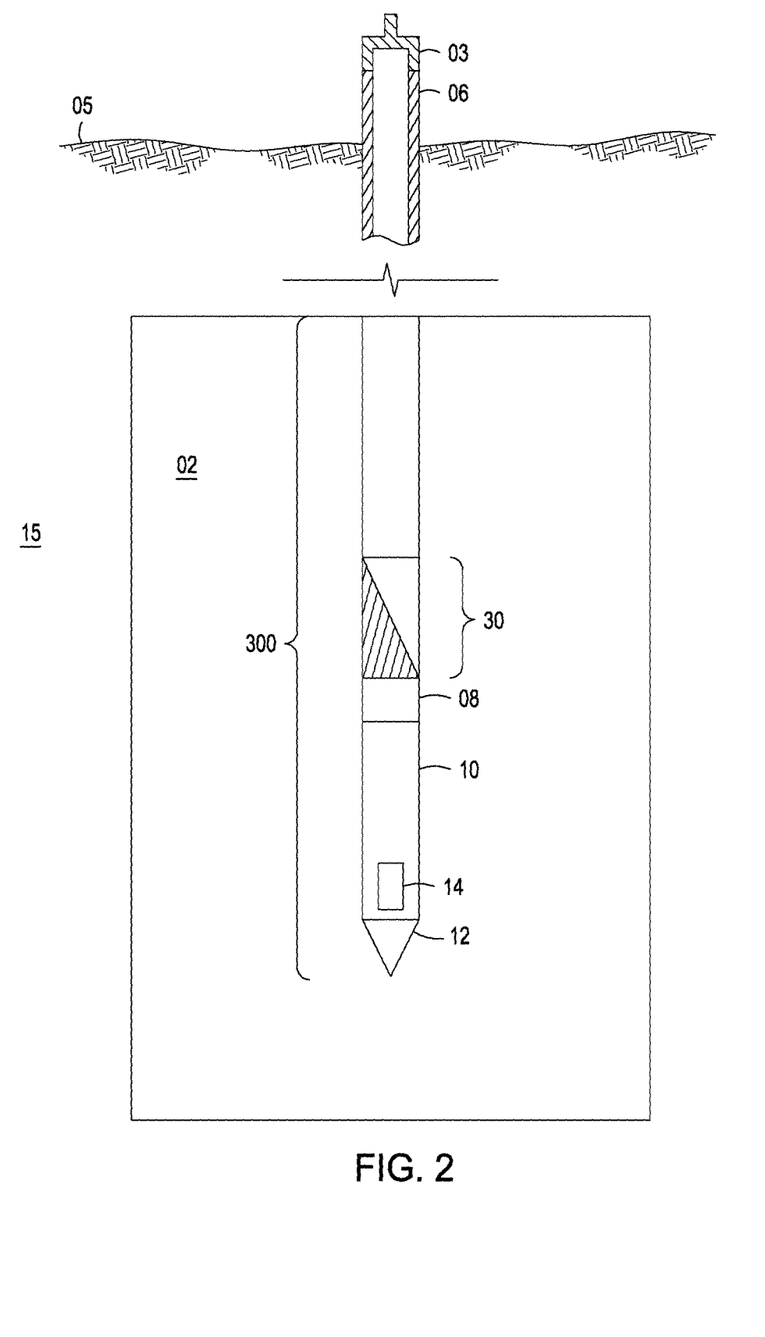
FIG. 2 is a side view of a cone penetrometer of the present invention, in one embodiment. Here, the wire of the cone penetrometer of FIG. 1 has been removed. A tubular whipstock cell is now shown connected between the push rods and a cone there below.

FIG. 2 is a side view of a cone penetrometer 300 of the present invention, in one embodiment. The cone penetrometer 300 represents a CPT device capable of periodic soil sampling. Thus, the penetrometer 300 may be referred to herein as a soil sampling apparatus.

It can be seen that the wire of the penetrometer 100 of FIG. 1 has been removed. In addition, a tubular whipstock cell 30 is shown connected between the push rods 6 and lower elements. The illustrative tubular whipstock cell 30 is positioned vertically between the threaded connection 8 and the push rods 6. For sampling operations, the pictured apparatus 300 remains static within the soil strata 2 and there is no direction of movement.

Integral to the tubular whipstock cell 30 is a beveled whipstock 32 and a sampling window 34. The window 34 is a window that has been pre-formed into the whipstock cell 30 adjacent the whipstock 32.

Figure 7A:
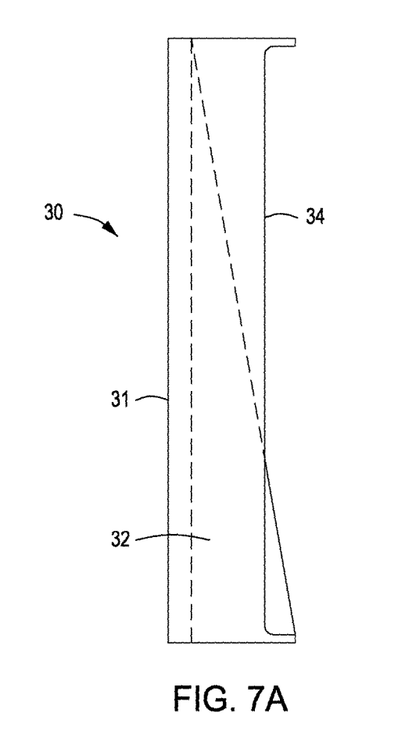
FIG. 7A is a side view of a tubular whipstock cell of the cone penetrometer, in one embodiment.
Figure 7B:
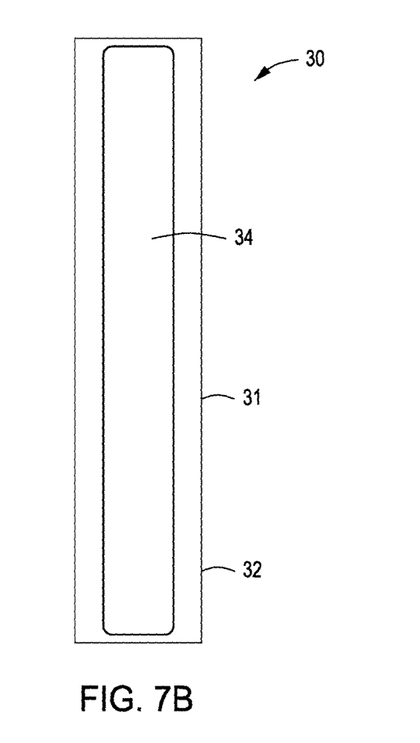
FIG. 7B is a front view of the whipstock cell of FIG. 7A.
Figure 7C:
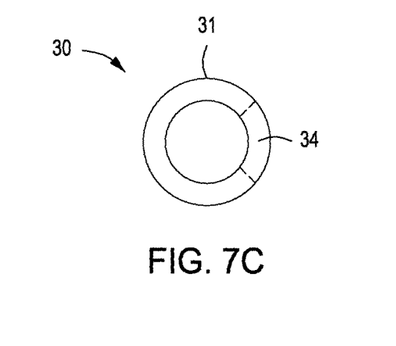
FIG. 7C is a top plan view of the whipstock cell of FIG. 7A.

FIG. 7A is a side view of the whipstock cell 30, in one embodiment. The whipstock cell 30 is shown in isolation for illustrative purposes. FIG. 7B is a front view of the whipstock cell 30, looking into the window 32. FIG. 7C is a top view of the whipstock cell 30. As can be seen, the whipstock cell 30 comprises a tubular housing 31, a beveled whipstock insert 32, and the sampling window 34.

Window 34 is comprised of an absence of material in the tubular housing 31. In an alternative embodiment, the window 34 may be concealed by a cover that can be opened, or may be comprised of a frangible material or a pliable material that will allow passage of the soil sampler 200 (described below) during sampling.

Figure 3:
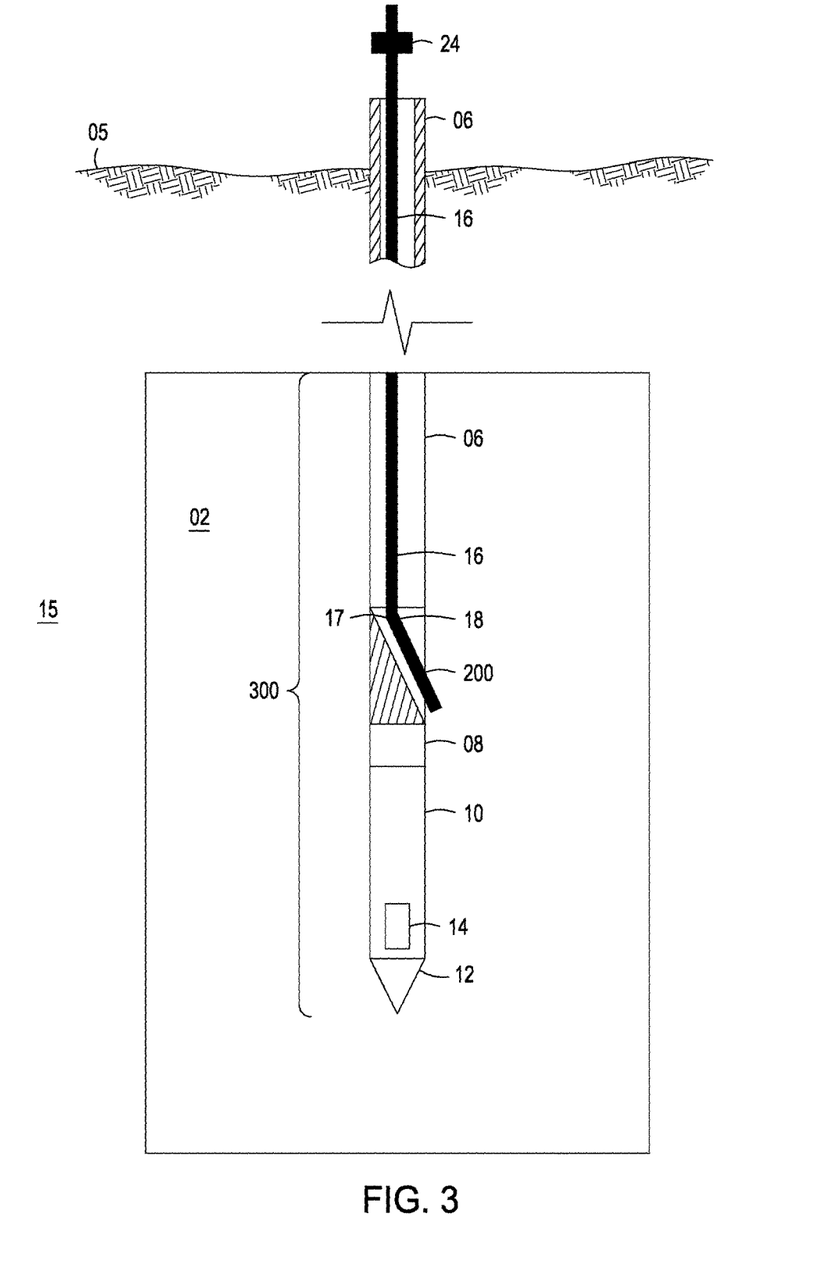
FIG. 3 is another side view of the cone penetrometer of FIG. 2. In this view, a sampling rod is slidably provided within the push rods. The sampling rod is used to support and run in a bent sub and a soil sampler.

FIG. 3 is another side view of the cone penetrometer 300 of the present invention. In this view, a series of sampling rods 16 is provided alongside the push rods 6. A bent sub 18 is provided at the distal end of the sampling rods 16. The bent sub 18 is formed at an angle offset from the longitudinal axis provided by the sampling rods 16. This enables the bent sub 18 to deflect off of the beveled whipstock insert 32 en route to the sampling window 34.

The sampling rods 16 are used to advance the bent sub 18 and a connected soil sampler 200 across the whipstock 32 and through the window 34. The sampling rods 16 are advanced into the soil strata 2 using a hydraulic ram 3, which may also be used to advance the push rods 6. The sampling rods 16 terminate at a distal end and support the bent sub 18 and the soil sampler 200. In the view of FIG. 3, a series of sampling rods 16 with a bent sub 18 and soil sampler 200 are shown being advanced through the tubular whipstock cell 30. The soil sampler 200 is operatively connected at the end of the bent sub 18.

Of note, the soil sampler 200 is inclined by the bent sub 18 at an angle from the longitudinal axis of the sampling rods 16. This angle is preferably the same as an angle provided by the face of the beveled whipstock insert 32. In one aspect, the whipstock 32 has a concave face or, alternatively, a flat face. The whipstock 32 is angled at between 2 degrees and 35 degrees from vertical. The angle of the face of the whipstock 32 from vertical is geometrically determined by the inner diameter of the push rods 6, the outer diameter of the soil sampler 200, the length of the soil sampler 200, and the length of the sampling window 34.

A first connection 17 is provided between the sampling rods 16 and the bent sub 18. Preferably, this is a fixed connection aligned vertically with the bent sub 18. A second connection at the distal end of the bent sub 18 is provided to a terminal hollow extruded element. This element may be a circle extruded to a cylinder. This is described further below in connection with the FIG. 5B series of drawings.

In a first embodiment (described more fully below in connection with FIG. 5B-1), the bent sub 180 is flexible so as to comply with an angle according to the whipstock insert 32. In a second embodiment (described below in connection with FIG. 5B-2), the bent sub 182 comprises a ball-and-socket bent sub 182. In a third embodiment (described below in connection with FIG. 5B-3) a serial cylinder bent sub 184 is employed. In a fourth embodiment (described below in connection with FIG. 5B-4) a bi-axially pinned bent sub 186 is employed. In any arrangement, this angle is induced in the bent sub 180, 182, 184 or 186 by the angle of the beveled whipstock insert 32 itself.

Figure 4:
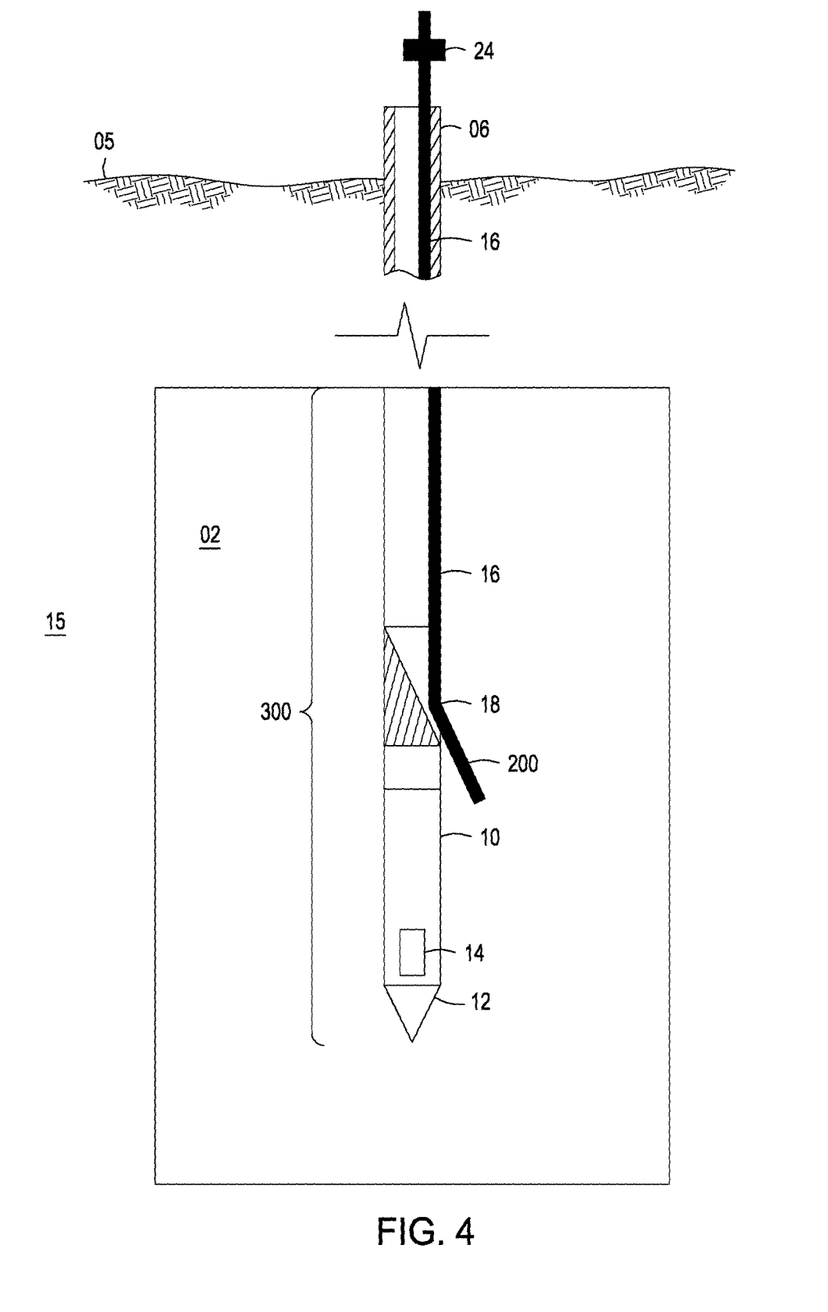
FIG. 4 is another side view of the cone penetrometer of FIG. 3. However, in this view a soil sampler has been advanced into a soil deposit so as to take a soil sample. Thus.

FIG. 4 is another side view of the cone penetrometer 300 of FIGS. 2 and 3. In this view, the soil sampler 200 has been advanced into a soil strata 2 at the zone 15 under study so as to take a sample. It is observed that the series of sampling rods 16 with the bent sub 18 and the soil sampler 200 have been advanced relative to the string of push rods 6. As the sampling rods 16 and connected soil sampler 200 are advanced, a normal force is applied on the face of the whipstock 32. Engaging both tension through the push rods 6 and compressive forces from the sampling rods 16, the string of push rods 6 and beveled whipstock 32 also apply a reactive force on the soil sampler and 20 and bent sub 18 such that the soil sampler 200 is advanced into the soil strata 2.

As the soil sampler 200 is advanced into relatively stationary soil strata 2, grains of soil are encapsulated within the walls of the soil sampler 200. In addition, the soil strata 2 will exert a reaction force upon the soil sampler 200, the bent sub 18, and the sampling rods 16 that is measurable through the sampling rods 16 and is transmitted to a sensor element 24. The data representing these forces may be used for engineering evaluation of the mechanical strength of the soil strata 2, independent of the data produced by friction sleeve 10, cone tip 12, or subsequent engineering analyses performed on soil grains from soil sampler 200.

Once grains of soil have been encapsulated within the walls of the soil sampler 200, tension can be applied to the sampling rods 16 to remove them to the surface 5. The connected bent sub 18 and soil sampler 200 are thus retrieved from the cone penetrometer 300. Intergranular forces and hoop stress may contribute to the retention of soil grains within the soil sampler 200. Thus, in certain embodiments, other known mechanical devices such as liners or retainers may be used to assist with retention of soil grains within the soil sampler 200.

Figure 5A:
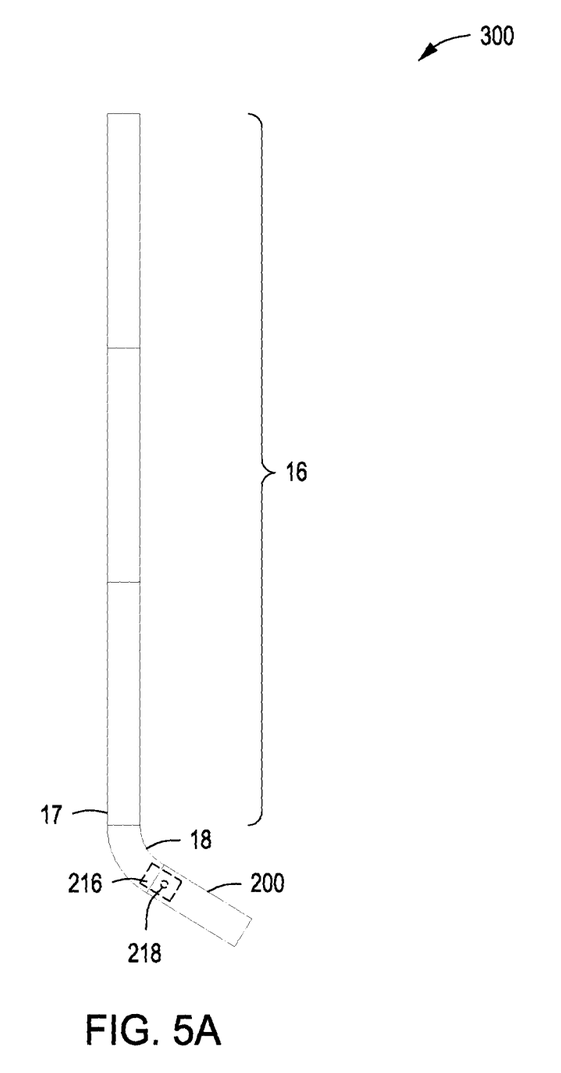
FIG. 5A is a schematic side view of the sampling apparatus that is part of the cone penetrometer of FIG. 3.

Once the soil sampler 200 has been removed from the cone penetrometer 300 and brought to the surface, grains from the soil strata 2 may be extruded or otherwise removed for engineering analyses. Engineering analyses that may be possible include but are not limited to:

ASTM D 2488—Standard Practice for Description and Identification of Soils (Visual-Manual Procedure)
ASTM D 2216—Standard Test Method for Laboratory Determination of Water (Moisture) Content of Soil, Rock, and Soil-Aggregate Mixtures
ASTM D 2974—Standard Test Methods for Moisture, Ash, and Organic Matter of Peat and Organic Soils
ASTM D 2937-00—Standard Test for Density of Soil in Place by the Drive-Cylinder Method
ASTM D 854-00—Standard Test for Specific Gravity of Soil Solids by Water Pycnometer
ASTM D 422—Standard Test Method for Particle-Size Analysis of Soils
ASTM D 4318—Standard Test Method for Liquid Limit, Plastic Limit, and Plasticity Index of Soils FIG. 5A is a schematic side view of the cone penetrometer sampling apparatus 300 of FIG. 3. The sampling apparatus 300 includes the sampling rods 16, the bent sub 18 and the soil sampler 200. In addition, FIG. 5B shows four alternate embodiments 180, 182, 184 and 186 for the bent sub 18. These are presented as FIGS. 5B-1, 5B-2, 5B-3 and 5B-4. The embodiments represent a flexurally bent sub 180, a ball and socket bent sub 182, a serial cylinder bent sub 184 and a bi-axially pinned bent sub 186. A commonality of the four embodiments of the bent sub 18 is that there are connections to the sampling rods 16 at a proximal end above, and to the soil sampler 200 at a distal end below.

Figure 5B:
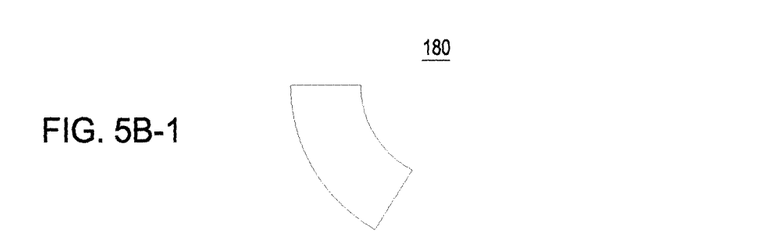

The first embodiment of the bent sub 18 is the flexurally bent sub 180. This is shown in FIG. 5B-1 at 180. The flexurally bent sub 180 is a continuous cylindrical element comprised of a plastic tubular material that may be bent to match the angle of the beveled whipstock insert 32 upon changes in force from the sampling rods 16. Alternatively, it may have an integrated fixed angle that does not substantially change with changes in force from the sampling rods 16 or the soil strata 2 or interaction with the beveled whipstock insert 32.

Figure 5B:
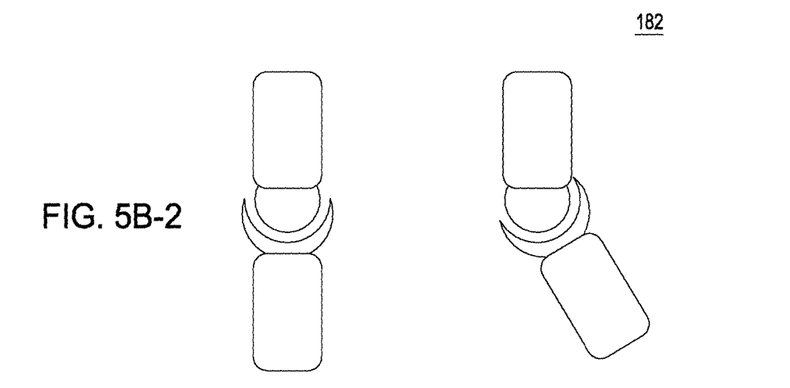

The second embodiment of the bent sub 18 is the ball-and-socket bent sub. This is shown at FIG. 5B-2 at 182. The ball and socket bent sub 182 comprises a ball joint and then a rigid leg extending there below. The ball and socket bent sub 182 may be comprised of one or more serial ball-and-socket joints, which may be connected internally by pins or a cable threaded through an integral boring within the balls and sockets, or connected externally via a tubular housing element. In FIG. 5B-2, the ball-and-socket bent sub 182 is shown moving from a vertical orientation to an angular deviation orientation in accordance with the angle of the whipstock insert 32.

Figure 5B:
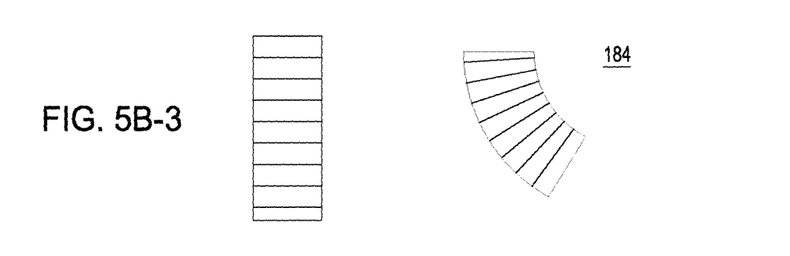

The third embodiment of the bent sub 18 is the serial cylinder bent sub. This is seen at FIG. 5B-3 at 184. The serial cylinder bent sub 184 comprises a series of short cylinders or, optionally, polygons, having flex connections, such as pins that enable limited angular travel. The cylinders may be connected internally by a cable threaded through an integral boring within the cylinders, or connected by a series of ridges and cavities on the outside of the cylinders, or connected externally via a tubular housing element. In FIG. 5B-3, the serial cylinder bent sub 184 is shown moving from a vertical orientation to an angular deviation orientation in accordance with the angle of the whipstock insert 32.

Figure 5B:
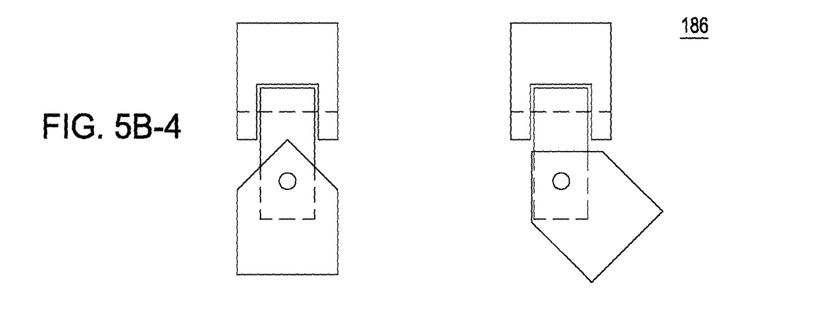

The fourth embodiment of the bent sub 18 is the bi-axially pinned bent sub. This is seen at FIG. 5B-4 at 186. The bi-axially pinned bent sub 186 comprises a central block joined to two connecting blocks by pins. The pins are oriented perpendicular to each other, and both pins are perpendicular to the vertical direction. In FIG. 5B-4, the bi-axially pinned bent sub 186 is shown moving from a vertical orientation to an angular deviation orientation in accordance with the angle of the whipstock insert 32.

The ball-and-socket bent sub 182, the serial cylinder bent sub 184 and the bi-axially pinned bent sub 186 are multi-component elements that enable limited angular bending depending upon the magnitude of force exerted from the sampling rods 16 and the soil strata 2, as well as the amount of force and angle of force exerted upon them and the soil sampler 200 from the beveled whipstock insert 32.

Figure 6:
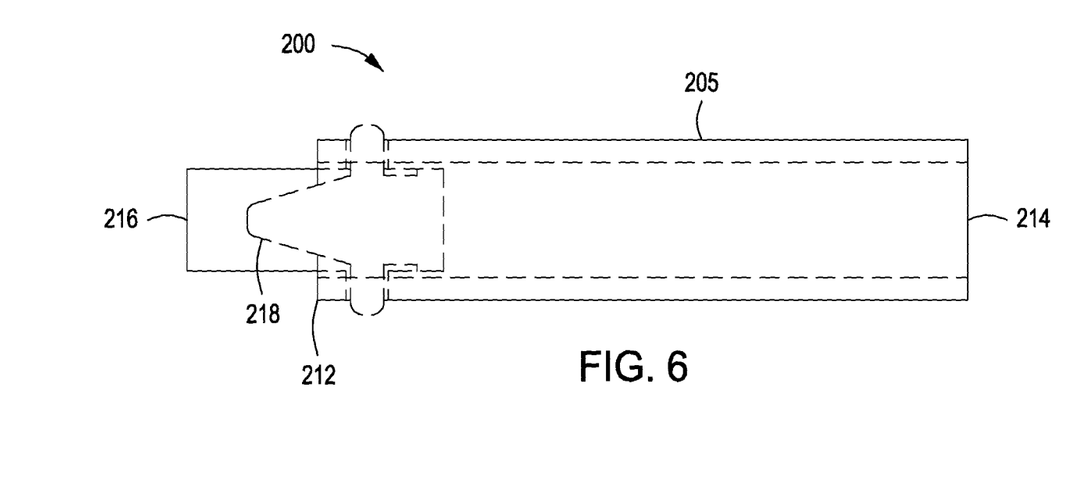
FIG. 6 is a cross-sectional view of a soil sampler, with apparatus to connect to sampling rods.

FIG. 6 presents a cross-sectional view of an illustrative soil sampler 200. The soil sampler 200 comprises a hollow tubular body 205. The body 205 has a proximal 212 and a distal end 214. The distal end 214 serves as a shearing element to separate soil from a soil strata 2 during use. The proximal end 212 is designed to be connected to the bent sub 18 by means of a connector sub 216 and a spring clip 218. Two holes are drilled in the proximal end 212 to admit protrusions from the spring clip 218 to fit therein.

In operation, the connector sub 216 is adhered to the distal end of the bent sub 18. The spring clip 218 utilizes spring force to maintain dual protrusions extending through holes drilled in the connector sub 216. These protrusions of the spring clip 218 may be forced slightly inward to allow admittance of the connector sub 216 within the distal end 212 of the soil sampler 200. Upon admittance, the protrusions of the spring clip 218 are allowed to extend naturally outward so as to create a shear connection between the connector sub 216 and the soil sampler 200.

During operation, intergranular forces and hoop stress may contribute to the retention of soil grains within the soil sampler 200. In certain embodiments, other mechanical devices such as liners or retainers may be used to assist with retention of soil grains within the soil sampler 200.

In a preferred embodiment, a 36 mm outer diameter cone tip 12 is progressed through a soil strata 2 using an embedded digital data cache 14 to store data. The soil sampler 200 is advanced using the bi-axially pinned bent sub 186 connected to sampling rods 16. Soil grains are sampled from soil strata 2, and the soil sampler 200 is retracted from the tubular whipstock cell 30 and push rods 6. During sampling, force data is recorded in the sensor element 24 and may later be compared to data stored in the digital data cache 14. This process is repeated at several intervals or depths within the soil strata 2.

In an alternative embodiment, a 44-mm outer diameter cone tip 12 is used in place of a 36 mm outer diameter cone tip.

In an alternative embodiment, a borehole is created in a soil strata 2 with no sampling apparatus attached, as by means of a standard CPT or typical soil augers used for the SPT. Subsequent to the creation of the borehole, the tubular whipstock cell 30 is advanced at the end of the push rods 6 into a soil strata 2. The sampling rods 16, bent sub 18 and soil sampler 200 are used as in a preferred embodiment to take soil samples. Data collected from the CPT step may be confirmed.

In one aspect, the cone penetrometer 100 further comprises a wire 4 transmitting data from the cone tip 12 vertically up through the push rods 6 and to the surface. Allowance is made in the push rods 6 for a wire cavity. However, the CPT-enabled soil sampler itself in most embodiments does not rely upon a wire 4 and is compatible with wireless CPT or simply stores data in the cache 14.

As can be seen, a soil sampling apparatus 300 is provided that operates in conjunction with a cone penetrometer. The apparatus 300 utilizes a novel soil sampler that extends at an angle from a string of push rods. In operation, the apparatus produces soil samples upon which additional engineering tests may be conducted. Whole soil samples, or avulsive samples, may be taken that include liquid, solid and gaseous phase materials. In one aspect, the device contains removable sample inserts for soil, which is customizable to capture or store certain soil phases.

Of particular benefit, the soil sampling apparatus of the present invention, in certain embodiments, is capable of taking soil samples from multiple depth intervals with only one probing or "trip" prior to sampling. The apparatus utilizes compressive energy delivered from above the tested soil stratum to take soil samples. The apparatus enables sampling of soil already tested by the cone tip and friction sleeve of a cone penetrometer, which may aid in the selection of which depth intervals to sample.

In one aspect, the bent sub is capable of transmitting compressive and tensile force vectors in one axis to compressive and tensile force vectors in an alternative axis. This change in force direction is done by normal force interaction between the soil sampler and the whipstock face 32, and the soil sampler 20 and the sampling window 34.

Of interest, the soil sampling apparatus is capable of sampling from either a vertical or inclined borehole. The apparatus further allows for either a bottom-up or a top-down sampling sequence.

It will be appreciated that the inventions are susceptible to modification, variation and change without departing from the spirit thereof.

The invention claimed is:

1. An apparatus for taking soil samples from subsurface soil strata, comprising:
   an elongated tubular whipstock cell having a proximal end and a distal end;
   a through-opening along a portion of the whipstock cell comprising a pre-formed window;
   a whipstock residing within the whipstock cell, the whipstock having a face angled towards the pre-formed window;
   at least one push rod connected to the proximal end of the whipstock cell, the push rod representing a tubular body;
   an elongated sampling rod dimensioned to be slidably moved through an inner diameter of the at least one push rod en route to the whipstock cell;
   a mechanical soil sampler configured to extend through the pre-formed window; and
   a bent sub having a proximal end and a distal end, wherein the proximal end is connected to a distal end of the sampling rod, and the distal end is connected to the soil sampler, and wherein the bent sub is configured to deflect off of the whipstock face when urged through the pre-formed window.

2. The soil sampling apparatus of claim 1, further comprising:
   a cone penetrometer residing at or below a distal end of the whipstock cell, the cone penetrometer comprising a conical tip and a friction sleeve.

3. The soil sampling apparatus of claim 2, wherein the at least one push rod comprises a plurality of hollow rods threadedly connected end-to-end.

4. The soil sampling apparatus of claim 2, wherein the at least one sampling rod comprises a plurality of rods threadedly connected end-to-end, and having an outer diameter that is smaller than an inner diameter of the at least one push rod.

5. The soil sampling apparatus of claim 2, wherein the bent sub comprises (i) a substantially straight cylindrical body fabricated from a pliable material capable of bending in response to angular forces, (ii) at least one ball-and-socket joint and a rigid leg such that the rigid leg may be deflected to a limited angular deviation when the soil sampler is pushed into contact with the face of the whipstock, (iii) a plurality of cylindrical bodies connected in series that permit limited angular deviation when the soil sampler is pushed into contact with the face of the whipstock, or (iv) a bi-axially pinned connection comprised of a center block and two connecting blocks that permits limited angular deviation when the soil sampler is pushed into contact with the face of the whipstock.

6. The soil sampling apparatus of claim 2, further comprising:
one or more sensors for sensing a soil condition, wherein the one or more sensors comprise a strain gauge, a moisture sensor, or a pore pressure sensor; and
the sensing device resides along (i) the whipstock cell, (ii) the friction sleeve or (iii) the sampling device.

7. The soil sampling apparatus of claim 6, further comprising:
a data cache for storing data generated by the one or more sensors.

8. The soil sampling apparatus of claim 7, wherein movement of the soil sampler through the window and into a soil strata produces a reaction force from soil shearing, which creates data which may be measured by a sensor and used in the analysis of soil deposits.

9. The soil sampling apparatus of claim 2, further comprising:
one or more sensors for sensing a soil condition, wherein the one or more sensors comprise a strain gauge, a moisture sensor, or a pore pressure sensor; and
a data cache for storing data generated by the one or more sensors;
wherein the sensing device and the data cache reside along the friction sleeve.

10. The soil sampling apparatus of claim 2, wherein the window is fabricated from a frangible material or a pliable material that breaks in response to the soil sampler moving through the pre-formed window in response to a compressive force applied to the sampling rod.

11. The soil sampling apparatus of claim 2, wherein the bent sub is capable of transmitting compressive and tensile force vectors in one axis to compressive and tensile force vectors in an alternative axis.

12. The soil sampling apparatus of claim 11, wherein the face of the whipstock has a concave face and is angled at between 2-degrees and 35-degrees from vertical.

13. A method of taking samples from subsurface soil, comprising:
providing an apparatus for taking soil samples, comprising:
an elongated tubular whipstock cell having a proximal end and a distal end;
a through-opening along a portion of the whipstock cell comprising a pre-formed window;
a whipstock residing within the whipstock cell, the whipstock having a face angled towards the pre-formed window;
at least one push rod connected to the proximal end of the whipstock cell, the push rod representing a tubular body; and
a cone penetrometer residing at or below a distal end of the whipstock cell, the cone penetrometer comprising a conical tip and a friction sleeve;
applying a downward force to the at least one push rod and connected whipstock cell and cone penetrometer;
continuing to apply the downward force to the at least one push rod and connected whipstock cell and cone penetrometer in order to drive the apparatus for taking soil samples into a subsurface zone of study at a first location;
running an elongated sampling rod into an inner diameter of the at least one push rod en route to the whipstock cell, wherein a bent sub is connected to a distal end of the at least one sampling rod, and a soil sampler is connected to a distal end of the bent sub;
continuing to run the sampling rod and connected bent sub into the at least one push rod until the mechanical soil sampler extends at least partially through the pre-formed window at the first location;
capturing a first soil sample from the soil within the zone of study; and
removing the sampling rod and connected bent sub and soil sampler from within the at least one push rod.

14. The method of claim 13, wherein:
the bent sub has a proximal end and a distal end, wherein the proximal end is connected to a distal end of the sampling rod, and the distal end is connected to the soil sampler; and
the soil sampler is configured to deflect off of the whipstock face when urged through the pre-formed window, and the bent sub is configured to comply with the deflection to permit capturing the first soil sample from a soil strata.

15. The method of claim 14, wherein:
the at least one push rod comprises a plurality of hollow rods threadedly connected end-to-end;
applying the downward force to the at least one push rod comprises manually pushing down on it the hollow rods.

16. The method of claim 15, wherein the at least one sampling rod comprises a plurality of rods threadedly connected end-to-end, and having an outer diameter that is smaller than an inner diameter of the at least one push rod.

17. The method of claim 16, wherein the apparatus further comprises:
one or more sensors for sensing a soil condition, wherein the one or more sensors comprise a strain gauge, a moisture sensor, or a pore pressure sensor;
the sensing device resides along (i) the whipstock cell, (ii) the friction sleeve or (iii) the sampling device; and
a data cache for storing data generated by the one or more sensors.

18. The method of claim 16, wherein movement of the soil sampler through the window and into a soil strata produces a reaction force from soil shearing, which creates data which may be measured by a sensor and used in the analysis of soil deposits.

19. The method of claim 16, further comprising:
moving the whipstock cell to a second location within the zone of study after removing the bent sub and soil sampler from the window;
running the sampling rod and connected bent sub along the at least one push rod until the mechanical soil sampler extends at least partially through the pre-formed window at the second location and into the soil strata; and
capturing a second soil sample from the soil within the zone of study before removing the sampling rod and connected bent sub and mechanical soil sampler from the at least one push rod.

20. The method of claim 16, wherein the apparatus further comprising:
one or more sensors for sensing a soil condition, wherein the one or more sensors comprise a strain gauge, a moisture sensor, or a pore pressure sensor;
a data cache for storing data generated by the one or more sensors;
wherein the sensing device and the data cache reside along the friction sleeve and a cover configured to enclose the window when the whipstock cell is moved down into the zone of study.

21. The method of claim 15, wherein the bent sub comprises (i) a substantially straight cylindrical body fabricated from a pliable material capable of bending in response to angular forces, (ii) at least one ball-and-socket joint and a rigid leg such that the rigid leg may be deflected to a limited angular deviation when the soil sampler is pushed into contact with the face of the whipstock, or (iii) a plurality of cylindrical bodies connected in series that permit limited angular deviation when the soil sampler is pushed into contact with the face of the whipstock, or (iv) a bi-axially pinned arrangement of a central block and two connecting blocks that permits limited angular deviation when the soil sampler is pushed into contact with the face of the whipstock.

\* \* \* \* \*